United States Patent
Sasaki et al.

(10) Patent No.: US 6,312,420 B1
(45) Date of Patent: Nov. 6, 2001

(54) PANTS-TYPE DISPOSABLE DIAPER

(75) Inventors: Toru Sasaki; Nariaki Shimoe; Yoshinori Kumasaka; Toshifumi Otsubo; Yasushi Inoue, all of Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/298,216

(22) Filed: Apr. 23, 1999

(30) Foreign Application Priority Data

Apr. 24, 1998 (JP) ................................ 10-115573

(51) Int. Cl.$^7$ ....................................... A61F 13/15
(52) U.S. Cl. ................ 604/385.28; 604/385.27; 604/385.01
(58) Field of Search ............ 604/385.1, 385.2, 604/358, 385.01, 385.28, 385.27

(56) References Cited

U.S. PATENT DOCUMENTS

| | | | |
|---|---|---|---|
| 4,695,278 | * | 9/1987 | Lawson ................................. 604/385 |
| 4,738,677 | * | 4/1988 | Foreman .............................. 604/385 |
| 5,026,364 | * | 6/1991 | Robertson ........................... 604/385.1 |
| 5,397,318 | * | 3/1995 | Dreier ................................ 604/385.2 |
| 5,415,644 | * | 5/1995 | Enloe ................................. 604/385.2 |
| 5,476,458 | * | 12/1995 | Glaug et al. .......................... 604/378 |
| 5,599,338 | * | 2/1997 | Enloe ................................. 604/385.2 |
| 5,601,544 | | 2/1997 | Glaug et al. . |
| 5,883,028 | * | 3/1999 | Morman et al. ...................... 442/394 |
| 6,179,820 | * | 1/2001 | Fernfors .......................... 604/385.27 |

FOREIGN PATENT DOCUMENTS

| | | |
|---|---|---|
| 0 623 331 A2 | 11/1994 | (EP) . |
| 0 648 482 A2 | 4/1995 | (EP) . |
| 0761194A2 | * 8/1996 | (EP) ............................... 604/385.2 |
| 0 761 194 A2 | 3/1997 | (EP) . |
| 0 847 739 A2 | 6/1998 | (EP) . |
| 2 253 131 A | 9/1992 | (GB) . |
| 2 268 389 A | 1/1994 | (GB) . |
| 6-93901 | 11/1994 | (JP) . |
| 9-56746 | 3/1997 | (JP) . |

OTHER PUBLICATIONS

Copy of European Search Report dated Jun. 5, 2001.

* cited by examiner

*Primary Examiner*—Aaron J. Lewis
*Assistant Examiner*—Michael Bogart
(74) *Attorney, Agent, or Firm*—Baker & Daniels

(57) ABSTRACT

A pants-type disposable diaper includes a pants-type outer cover and an absorbent pad attached on an inner surface of the outer cover, the outer cover having first elastic members which circumferentially extend in the vicinity of a waist-opening of the outer cover and second elastic members which circumferentially extend in the vicinity of the uppermost points of a pair of leg-opening of the outer cover, the pad having an elongate pad body provided with a pair of barrier cuffs, the barrier cuffs having third elastic member at distal edges of the barrier cuff and fourth elastic members between the distal edges and proximal edges of the barrier cuffs, the fourth elastic member intersecting the second elastic members in front and rear waist regions of the outer cover.

6 Claims, 5 Drawing Sheets

PANTS-TYPE DISPOSABLE DIAPER

BACKGROUND OF THE INVENTION

The present invention relates to a pants type disposable diaper for absorbing and containing body exudates.

Japanese Patent Publication No. Hei6-93901 discloses a disposable diaper having a pair of gasket cuffs adapted to elastically contact around the legs of the wearer and a pair of barrier cuffs adapted to elastically contact against the perineum of the wearer. The barrier cuffs slant inwardly of the diaper and cooperate with the liquid-absorbent core to form channels within which body exudates are contained and held. The diaper is stabilized in its worn position by tightly placing the diaper around the waist regions and the legs of the wearer.

Japanese Patent Application Disclosure Gazette No. Hei9-56746 discloses a disposable diaper comprising a pants-type cover member and a liquid-absorbent pad attached to an inner side of the cover member and longitudinally extending across a crotch region of the cover member into front and rear waist regions of the cover member. The liquid-absorbent pad is provided along its transversely opposite side edges with elastic member secured thereto with longitudinal tension, i.e., directed towards the front and rear waist regions. The cover member is provided in the vicinity of the waist-opening and in the vicinity of the uppermost points of the respective leg-openings with elastic members circumferentially extending in the waist regions. The crotch region of the cover member is longitudinally stretchable, i.e., towards the front and rear waist regions.

In the case of the diaper disclosed in the foregoing Japanese Patent Publication No. Hei6-93901, it is essential to press the pair of gasket cuffs formed along transversely opposite sides of the diaper around the legs of the wearer. Therefore it is difficult to limit a distance between the pair of gasket cuffs even when a distance between the pair of barrier cuffs serving to hold body exudates is relatively short. Necessarily, the crotch region must be relatively wide and bulky. As a result, the diaper may create a feeling of discomfort against the wearer.

The diaper disclosed in Japanese Patent Application Disclosure Gazette No. Hei9-56746 does not require the gasket cuffs in order to achieve fitting of the diaper around the legs of the wearer, so that there is no apprehension that the width of the crotch region may be excessively wide. However, the diaper is disadvantageous in that side edges of the liquid-absorbent pad merely extending outwards can not form a pair of channels adapted to be opened inwardly. When a large amount of body exudates flows towards the side edges, it is difficult for the diaper to prevent body exudates from leaking sideways. Even if the side edges of the diaper are provided with channels, the elastic crotch region is pressed against the crotch of the wearer and consequently the channels are closed. Thus, the channels are substantially useless.

SUMMARY OF THE INVENTION

In view of the problems been described above, it is an object of the present invention to provide a disposable diaper which allows a width of the crotch region to be limited without loss of its effective function to avoid sideways leakage of body exudates.

According to the present invention, a pants-type disposable diaper comprising a pants-type outer cover having a front waist region, a rear waist region and a crotch region extending between the front and rear regions, the front waist region being connected to the rear waist region along transversely opposite side edges of them to form a waist-opening and a pair of leg-openings, and a liquid-absorbent pad member attached to an inner side of the outer cover and extending across the crotch region into the front and rear waist regions, wherein:

the outer cover member has first elastic members circumferentially extending under tension in the vicinity of the waist-opening; and second elastic members circumferentially extending under tension in the vicinity of the uppermost points of the pair of leg-openings, the liquid-absorbent pad has an elongate pad body comprising a liquid-pervious topsheet, a liquid-impervious backsheet and a liquid-absorbent core disposed between the topsheet and the backsheet; and a pair of barrier cuffs comprising proximal edges longitudinally extending along transversely opposite side edges of the core integrally with portion of the backsheet extending laterally beyond the side edges of the core and distal edges extending in parallel to the proximal edges and risably collapsing onto an inner side of the pad body to partially cover the topsheet; the pad body has an outer surface thereof at longitudinally opposite ends thereof joined to the inner side of the outer cover in the front and rear waist regions between the ones of the first elastic members lying adjacent the waist-opening and the ones of the second elastic members lying adjacent the pair of leg-openings, respectively; the barrier cuffs, in a state of collapsed onto the inner side of the pad body, have inner surfaces at the longitudinally opposite ends of the barrier cuffs joined to the topsheet; third elastic members longitudinally extending under tension along respective ridges of the distal edges and fourth elastic members longitudinally extending under tension between the proximal edges and the distal edges; and at least respective ones of the fourth elastic members intersect the second elastic members in the front and rear waist regions.

According to an embodiment of the present invention, the first and second elastic members extend around the waist regions substantially in a horizontal direction of the outer cover.

According to another embodiment of the present invention, the second elastic members circumferentially extending around the waist regions describe, in a transversely middle zone of at least one of the front and rear waist regions, a curve which is convex towards the crotch region.

According to still another embodiment of the present invention, the backsheet is made of a plastic film and the barrier cuffs are made of a nonwoven fabric.

According to further another embodiment of the present invention, the barrier cuffs are made of a substantially liquid-impervious material.

According to further additional embodiment of the present invention, the outer cover is made of a breathable nonwoven fabric.

DETAILED DESCRIPTION OF THE PREFERRED EMBODIMENTS

Details of a pants-type disposable diaper according to the present invention will be more fully understood from the description given hereunder with reference to the accompanying drawings.

Figure 1:
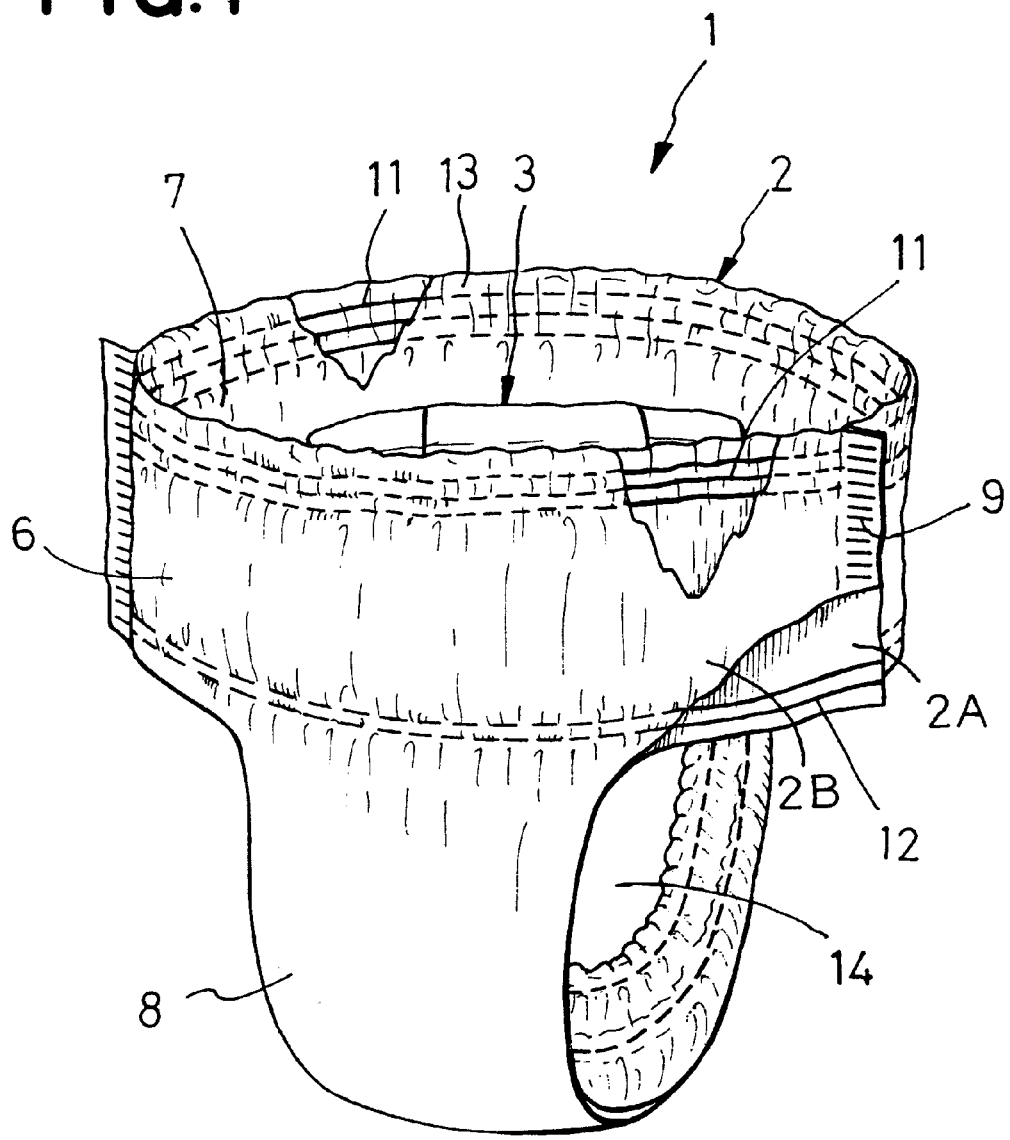
FIG. 1 is a perspective view of a partly cutaway pants type diaper constructed according to the present invention.

Diaper 1 shown by FIG. 1 in a perspective view as partly cutaway comprises a pants-type outer cover 2 and liquid-absorbent pad 3 attached to the inner surface of the outer cover 2.

The outer cover 2 comprises inner and outer sheets 2A, 2B bonded to each other, a front waist region 6, a rear waist region 7 and a crotch region 8 extending between these two waist regions 6, 7. The front and rear waist regions 6, 7 have transversely opposite side edges, respectively, placed flat upon each other and joined together at spots 9 intermittently arranged along the respective side edges to form a waist-opening 13 and a pair of leg-openings 14. In the front and rear waist regions 6, 7, a plurality of first elastic members 11 circumferentially extend under appropriate tension substantially all around the diaper 1. In proximity of the uppermost points of the leg-openings 14, a plurality of second elastic members 12 also circumferentially extend under appropriate tension substantially all around the diaper 1. The description herein given "extend substantially all around the diaper 1" means that the first elastic members as well as the second elastic members extending in the front waist region have their transversely opposite ends overlapping or lying closely adjacent corresponding ends of the first and second elastic members, respectively, extending in the rear waist region in proximity of the transversely opposite side edges of the diaper 1.

Figure 2:
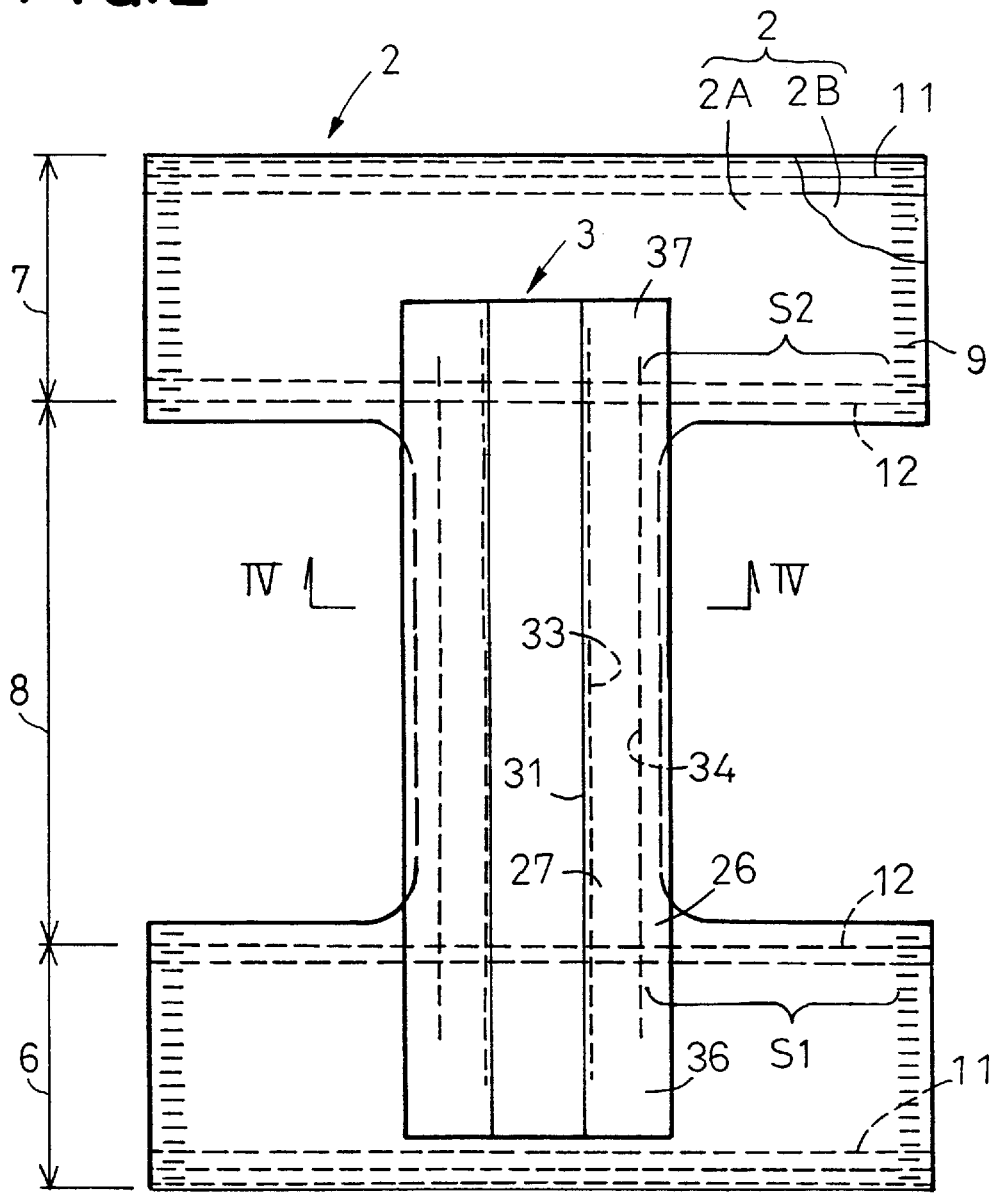
FIG. 2 is a plan view of the developed diaper of FIG. 1.
Figure 3:
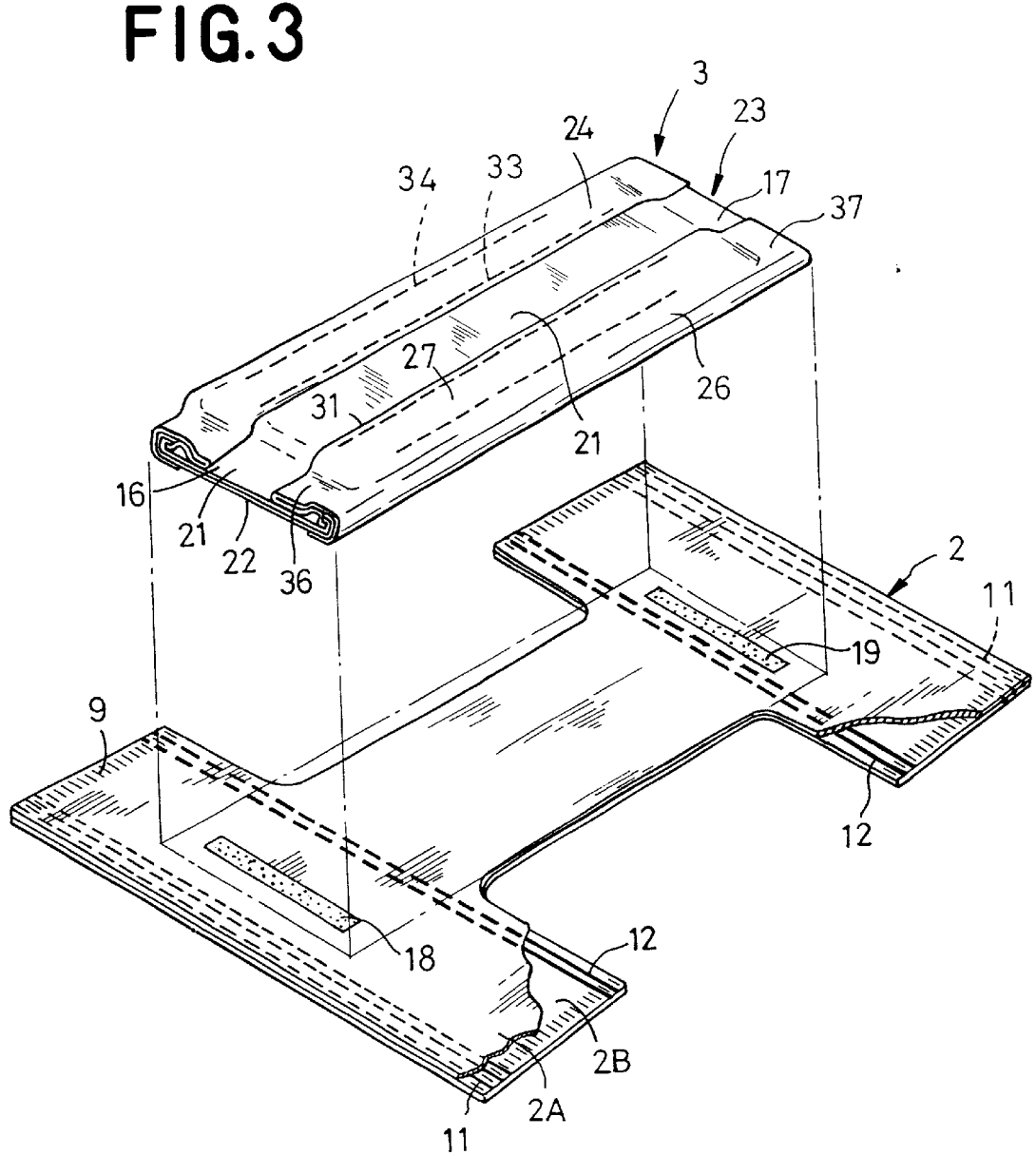
FIG. 3 is an exploded perspective view of the diaper of FIG. 2.

FIG. 2 is a plan view of the diaper 1 of FIG. 1 as having been developed longitudinally and transversely thereof after the front and rear waist regions were separated from each other at the intermittent bonding spots 9 and FIG. 3 is an exploded perspective view showing this diaper 1. The inner and outer layer sheets 2A, 2B forming the outer cover 2 may be made of a nonwoven fabric or a plastic film. The layer sheets 2A, 2B may be breathable or non-breathable and liquid-pervious or liquid-impervious. The inner layer sheet 2A and the outer layer sheet 2B are bonded together by means of hot melt adhesive or heat-sealing. In the front and rear waist regions 6, 7, the first and second elastic members 11, 12 are disposed between the inner and outer layer sheets 2A, 2B and bonded to the inner surface of at least one of these two layer sheets 2A, 2B. Transversely opposite side edges of the crotch region 8 are concavely curved to form the pair of leg-openings 14.

The liquid-absorbent pad 3 longitudinally extends across the crotch region 8 into the front and rear waist regions 6, 7 and has its longitudinally opposite ends 16, 17 joined to the inner surface of the cover member 2 over zones 18, 19, respectively, by means of hot melt adhesive. These joining zones 18, 19 respectively lie between the uppermost one of the first elastic members 11 extending in proximity of the waist opening 13 and the lowermost one of the second elastic members 12 extending in proximity of the uppermost peripheral edges of the leg-openings 14. The liquid-absorbent pad 3 comprises an elongate pad body 23 having its bottom surface covered with the liquid-impervious backsheet 22 and a pair of barrier cuffs 24 longitudinally extending along transversely opposite side edges of the pad body 23. As shown, each of the barrier cuffs 24 has a proximal edge 26 joined to the pad body 23 and a distal edge 27 extending in parallel to the proximal edge 26. The barrier cuff 24 is folded inwardly of the pad body 23 in proximal edge 26 so that the distal edge 27 and a part of the barrier cuffs 24 in the vicinity of the distal edge 27 may collapse onto the pad body 23 and partially cover the topsheet 21 of the pad body 23. Longitudinally opposite ends 36, 37 of the distal edge 27 are joined to the topsheet 21. The barrier cuff 24 includes at least one third elastic member 33 extending along a ridge 31 of the distal edge 27 and at least one fourth elastic member 34 longitudinally extending between the proximal edge 26 and the distal edge 27, preferably in proximal edge 26. As will be apparent from FIG. 2, the fourth elastic member 34 intersects the second elastic member 12 extending circumferentially of the diaper 1.

Figure 4:
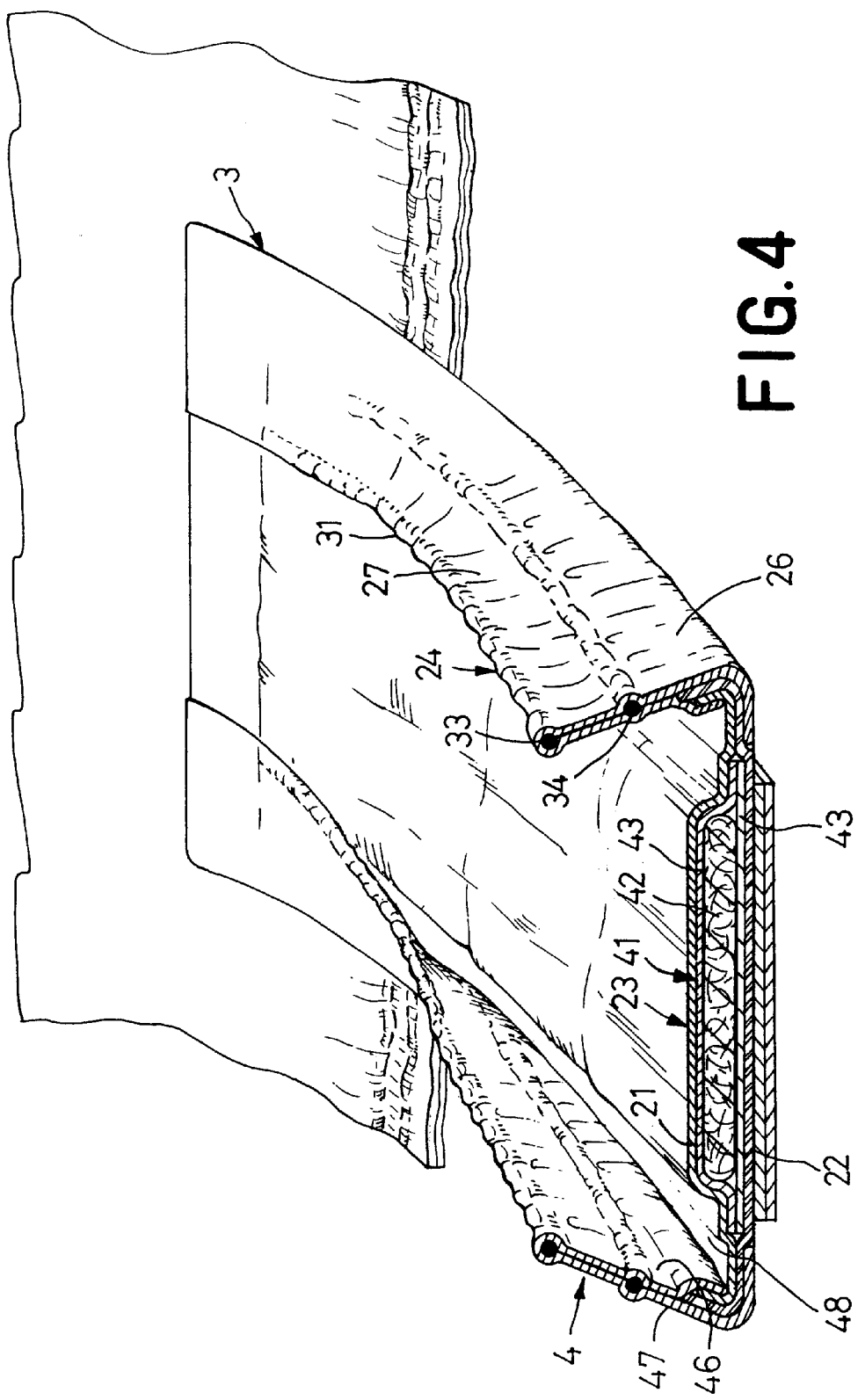
FIG. 4 is a fragmentary sectional view taken along line IV—IV in FIG. 2.

FIG. 4 is a fragmentary sectional view taken along line IV—IV in FIG. 2, in which the diaper 1 is slightly curved in its longitudinal direction with the liquid-absorbent pad 3 lying inside and the barrier cuffs 24 slightly rise on the topsheet 21. The pad body 23 comprises the topsheet 21 and the backsheet 22 and a liquid-absorbent core 41 disposed between these two sheets 21, 22. The core 41 comprises fluff pulp 42 or a mixture 42 of the fluff pulp and superabsorptive polymer particles having top and bottom surfaces covered with a tissue paper 43. The topsheet 21 and the backsheet 22 extend outwards beyond a peripheral edge of the core 41 and, in their respective extensions, the topsheet 21 and the backsheet 22 are placed flat upon each other and bonded together. The extension of the topsheet 21 is preferably selected to be the same as the extension of the backsheet 22 or shorter than the latter. The barrier cuff 24 comprises a substantially liquid-impervious sheet folded along the ridge 31 to define inner and outer sheet sections 46, 47 which are then placed upon each other and bonded together. The inner sheet section 46 is bonded to the topsheet 21 along the outer edge of the topsheet 21, on one hand, and bonded to the backsheet 22 along the outer edge thereof extending laterally beyond the outer edge of the topsheet 21, on the other hand. The outer sheet section 47 is bonded to the backsheet 22. The third elastic member 33 extending along the ridge 31 and the fourth elastic member 34 extending along the proximal edge 26 are secured to an inner surface of at least one of the inner and outer sheet sections 46, 47.

With the liquid-absorbent pad 3 constructed as has been described above, the third and fourth elastic members 33, 34 contract as the diaper 1 is curved longitudinally thereof. Thereupon, the distal edge 27 of each barrier cuff 24 pivotally rises around the proximal edge 26 on the upper surface of the pad body 23 at least in the crotch region 8. Consequently, a channel 48 formed between the barrier cuff 24 and the pad body 23 is fully opened. By laying the fourth elastic member 34 in the proximal edge 26, the second elastic members 12 in the front and rear waist regions of the diaper 1 can be intersected by the fourth elastic member 34 without significantly spacing these elastic members 12, 34 from each other in the vertical direction as viewed in FIG. 3. In the diaper 1 of such an arrangement, the fourth elastic member 34 cooperates with lengths S1, S2 of the second elastic members 12 defined between the fourth elastic member 34 and the side edges of the respective waist regions (See FIG. 2) to surround a wearer's leg in the vicinity of its base as if they were continuous elastic members. Therefore, the diaper 1 offers a good fitting around the wearer's legs without a demand for gasket cuffs which have usually been utilized. Because the gasket cuffs are absent, it is possible to avoid the inconvenience that the crotch region 8 may become excessively wide and/or bulky and, in cause, a feeling of discomfort against the wearer.

Figure 5:
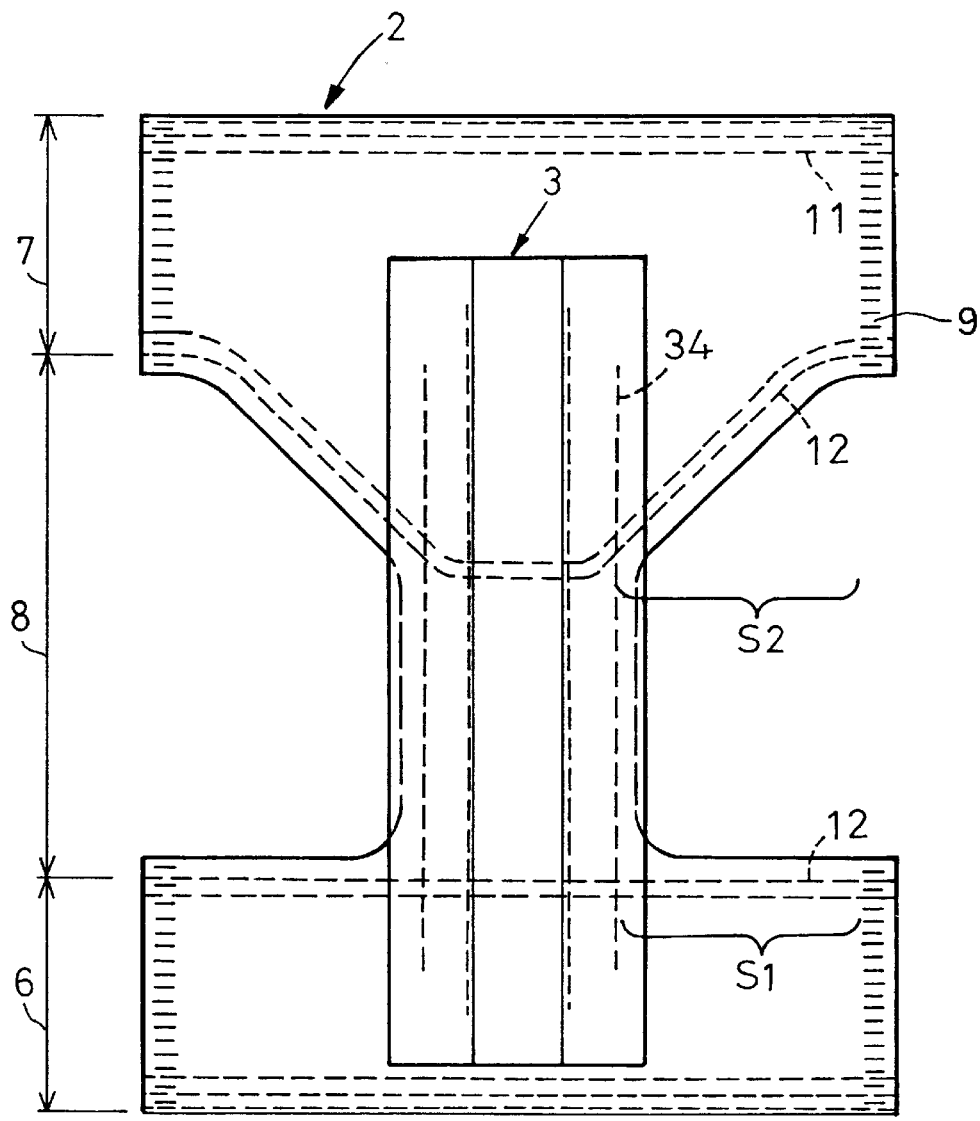
FIG. 5 is a view similar to FIG. 2 showing another embodiment of the present invention.

FIG. 5 is a view similar to FIG. 2 of another embodiment of the present invention. In the diaper 1, the second elastic members 12 extending across the rear waist region 7 describe in a transversely middle zone of the waist region 7 a curve which is convex towards the crotch region 8. Obliquely extending sections S2 of the second elastic members 21 as shown are more effective to surround the wearer's legs than in the case shown by FIG. 2. If it is desired, the second elastic members 12 in the front waist region 6 also may be laid so as to described a curve convex which is towards the crotch region 8.

The barrier cuff 24 may be made of substantially liquid-impervious material sufficient to be suitable for use as a component of the diaper 1. For example, the barrier cuff 24 may be made of a nonwoven fabric or a plastic film, preferably of a nonwoven fabric or a plastic film which is not only liquid-impervious but also breathable. Preferably, the nonwoven fabrics of thermoplastic synthetic fibers is used and, if necessary, such nonwoven fabric may be subjected to water repellent finish prior to its use. The barrier cuff 24 may be formed also by folding back a portion of the backsheet 22 adequately extending laterally beyond the pad body 23 onto the upper surface of the pad body 23. To bond the respective members of the diaper 1 to each other, a go suitable adhesive agent such as hot melt adhesive may be used. For the members which are of heat-sealable nature, the heat-sealing technique also may be utilized.

The disposable diaper according to the present invention allows the crotch region to be formed in a relatively narrow width because the pants-type outer cover has no elastic member associated with the leg-openings. Such crotch region ensures a good feeling when the diaper is worn. Furthermore, the elastic members circumferentially extending in the waist regions of the outer cover and the elastic members longitudinally extending in the barrier cuffs are arranged so that they intersect each other. Consequently, the diaper can tightly fit around the wearer's legs although the outer cover has no elastic exclusively associated with the leg-openings.

What is claimed is:

1. A pants-type disposable diaper comprising:

a pants-shaped outer cover having a front waist region, a rear waist region and a crotch region extending between said front and rear waist regions, said front waist region being connected to the rear waist region along transversely opposite side edges so as to form a waist-opening and a pair of leg-openings;

a liquid-absorbent pad attached to an inner side of said outer cover and extending across said crotch region into said front and rear waist regions, said liquid-absorbent pad including an elongate pad body comprising a liquid-pervious topsheet, a liquid-impervious backsheet and a liquid-absorbent core disposed between said liquid-pervious topsheet and said liquid-impervious backsheet;

first elastic members circumferentially extending under tension in a vicinity of said waist-opening;

second elastic members circumferentially extending under tension in a vicinity of uppermost portions of said pair of leg-openings;

a pair of barrier cuffs comprising:

proximal edges which extend along transversely opposite side edges of said liquid-absorbent core, said proximal edges being integral with a portion of said liquid-impervious backsheet which extends laterally beyond said side edges of said liquid-absorbent core; and distal edges which extend in parallel to said proximal edges and which are collapsible onto an inner side of said pad body to partially cover said liquid-pervious topsheet, said pad body having an outer surface with longitudinally opposite ends thereof being joined to the inner side of said outer cover in the front and rear waist regions between one of said first elastic members and one of said second elastic members, said pair of barrier cuffs having inner surfaces at said longitudinally opposite ends which are joined to said topsheet, said pants-type disposable diaper further comprising:

third elastic members which extend under tension along respective ridges of said distal edges; and fourth elastic members which extend longitudinally under tension between said proximal edges and said distal edges with one of said fourth elastic members intersecting said second elastic members in said front and rear waist regions.

2. The diaper according to claim 1, wherein said first and second elastic members extend from one of said transversely opposite side edges to the other around said front and rear waist regions substantially in a direction which is substantially perpendicular to said crotch region of said outer cover.

3. The diaper according to claim 1, wherein said second elastic members extend from one of said transversely opposite side edges to the other of said front and rear waist regions and define, in a transversely middle zone of at least one of said front and rear waist regions, a curve which is convex towards said crotch region.

4. The diaper according to claim 1, wherein said backsheet is made of a plastic film and said pair of barrier cuffs are made of a nonwoven fabric.

5. The diaper according to claim 1, wherein said pair of barrier cuffs are made of a substantially liquid-impervious material.

6. The diaper according to claim 1, wherein said outer cover is made of a breathable nonwoven fabric.

* * * * *